(12) United States Patent
Niemann et al.

(10) Patent No.: US 7,521,018 B2
(45) Date of Patent: Apr. 21, 2009

(54) DEVICE AND METHOD FOR DETECTING HARMFUL GASES USING A CARBON DIOXIDE SENSOR

(75) Inventors: Markus Niemann, Beckingen (DE); Thomas Sperlich, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 739 days.

(21) Appl. No.: 10/938,925

(22) Filed: Sep. 9, 2004

(65) Prior Publication Data
US 2005/0135966 A1 Jun. 23, 2005

(30) Foreign Application Priority Data
Dec. 20, 2003 (DE) ................. 103 60 217

(51) Int. Cl.
*G01N 21/00* (2006.01)
*B60H 1/00* (2006.01)
*G01N 35/08* (2006.01)
(52) U.S. Cl. ............... 422/62; 454/75; 436/55
(58) Field of Classification Search ........... 436/133; 454/69–162
See application file for complete search history.

(56) References Cited

U.S. PATENT DOCUMENTS 3,418,914 A * 12/1968 Finkin ................. 454/75
5,259,813 A * 11/1993 Abthoff et al. ........... 454/75

FOREIGN PATENT DOCUMENTS

DE 35 26 462 7/1990

* cited by examiner

*Primary Examiner*—Jill Warden
*Assistant Examiner*—Timothy G Kingan
(74) *Attorney, Agent, or Firm*—Kenyon & Kenyon LLP

(57) ABSTRACT

A device for controlling a ventilation system in the interior of a motor vehicle includes a gas concentration determining arrangement to determine the exterior concentration of a gas in the exterior air surrounding the vehicle and to determine the interior concentration of the same gas in the air contained in the interior of the vehicle, and an air flow control arrangement, via which the proportion of circulating air and the proportion of fresh air from the surroundings of the vehicle in the air delivered to the interior by the ventilation system are controlled as a function of the determined interior concentration or the determined exterior concentration. The gas concentration determining arrangement is represented by a single gas sensor.

10 Claims, 2 Drawing Sheets

DEVICE AND METHOD FOR DETECTING HARMFUL GASES USING A CARBON DIOXIDE SENSOR

FIELD OF THE INVENTION

The present invention relates to a device and method for detecting harmful gases using a carbon dioxide sensor.

BACKGROUND INFORMATION

German patent document no. 35 26 462 discusses a method for checking the air quality in motor vehicles using an internal and an external sensor in a moving or stationary vehicle. The fresh air flaps are either switched to circulating air or closed when a level of harmful substances detected by the external sensor is exceeded.

If the alarm is triggered, i.e., the level of harmful substances in the exterior air has exceeded a predefined value, the value of the interior sensor is logically compared with the value of the exterior sensor. If the air quality in the vehicle is poorer than the air quality outside the vehicle, the procedure is reversed, i.e., the flaps are switched to supply of exterior air.

SUMMARY OF THE INVENTION

The exemplary embodiment and/or exemplary method of the present invention relates to a device for controlling a ventilation system in the interior of a motor vehicle, containing
 a gas concentration determining arrangement for determining the exterior concentration of a gas in the exterior air surrounding the vehicle and for determining the interior concentration of the same gas in the air contained in the interior of the vehicle, and
 an air flow control arrangement, via which the proportion of circulating air and the proportion of fresh air from the surroundings of the vehicle in the air delivered to the interior by the ventilation system are controlled as a function of the determined interior concentration or the determined exterior concentration.

With the exemplary embodiment and/or exemplary method of the present invention, the gas concentration determining arrangement is represented by a single gas sensor. This makes a particularly cost-effective control of the ventilation system possible. It should be emphasized explicitly that the exemplary embodiment and/or exemplary method of the present invention refers both to vehicles and their ventilation systems having air conditioning systems and to vehicles and their ventilation systems without air conditioning systems.

Of course, values representing the exterior concentration and the interior concentration, referred to in the following as exterior value and interior value, may also be determined instead of the exterior concentration and the interior concentration.

The exemplary embodiment and/or exemplary method of the present invention is characterized by the fact that the gas sensor is situated in a part of the ventilation system through which both the fresh air supplied to the interior of the vehicle in fresh air mode and the circulating air circulated in the vehicle in recirculating mode flow. In this position, it is possible to determine the particular gas concentration in a particularly simple manner.

The exemplary embodiment and/or exemplary method of the present invention is characterized by the fact that the gas sensor is situated in the mixing chamber of the ventilation system. The mixing chamber is well suited for this purpose due to the compact design of the sensor.

The exemplary embodiment and/or exemplary method of the present invention is characterized by the fact that the air flow control arrangement is represented by the recirculating flap. This component is present in almost all vehicles.

The exemplary embodiment and/or exemplary method of the present invention is characterized by the fact that the gas sensor is represented by a carbon dioxide sensor. Monitoring this variable is particularly important because an increased carbon dioxide level in the interior air causes fatigue symptoms in the driver.

The exemplary embodiment and/or exemplary method of the present invention is characterized by the fact that the gas sensor is situated in such a way that it
 determines the interior concentration of the gas in recirculating mode of the ventilation system, and
 determines the exterior concentration of the gas in fresh air mode of the ventilation system.

The harmful substance concentration which is relevant in each case is thus determined in each operating state of the ventilation system.

The exemplary embodiment and/or exemplary method of the present invention is characterized by the fact that a query arrangement is available
 via which at least the determined interior concentration is analyzed in recirculating mode of the ventilation system and, as a function thereof, either the recirculating mode of the ventilation system is maintained or the ventilation system is switched over to fresh air mode, and
 via which at least the determined exterior concentration is analyzed in fresh air mode of the ventilation system and, as a function thereof, either the fresh air mode of the ventilation system is maintained or the ventilation system is switched over to recirculating mode.

This allows for, in the event of poor quality of the interior air or exterior air, switching the ventilation system to an appropriate mode resulting in an improvement in the air quality.

The exemplary embodiment and/or exemplary method of the present invention is characterized by the fact that
 in recirculating mode, the ventilation system is switched over to fresh air mode if the query arrangement determines that a first limiting value has been exceeded by the interior concentration, and
 in fresh air mode, the ventilation system is switched over to recirculating mode if the query arrangement determines that a second limiting value has been exceeded by the exterior concentration.

Querying for a limiting value having been exceeded is very easily implementable in a control unit.

The exemplary embodiment and/or exemplary method of the present invention is characterized by the fact that if
 in recirculating mode it is established that the first limiting value has been exceeded by the interior concentration and in the immediately following fresh air mode it is established that the second limiting value has been exceeded by the exterior concentration or
 in fresh air mode it is established that the second limiting value has been exceeded by the exterior concentration and in the immediately following recirculating mode it is established that the first limiting value has been exceeded by the interior concentration,
 the ventilation system
 is switched to fresh air mode if the determined exterior concentration is less than the determined interior concentration, and is switched to recirculating mode if the determined interior concentration is less than the determined exterior concentration, and it remains in this operating state for a predefined time period.

This is relevant in the case where both the exterior air and the interior air contain harmful substances. While the system remains in a particular operating state for a predefined time period, switchover of the recirculating flap is disabled. Periods of approximately 10 seconds or even a few minutes, for example, are conceivable as the time period. This means that a check may be performed at regular intervals to see whether the quality of the exterior air and the interior air continues to be poor.

The exemplary embodiment and/or exemplary method of the present invention furthermore includes a method for controlling the air conditioning system or the ventilation system in a vehicle in which the exterior concentration of a gas in the exterior air surrounding the vehicle is determined in an exterior determination, the interior concentration of the same gas in the interior of the vehicle is determined in an interior determination, and the proportion of circulating air and the proportion of fresh air from the surroundings of the vehicle in the air delivered to the interior by the ventilation system are controlled as a function of the determined interior concentration or the determined exterior concentration.

With the exemplary method according to the present invention, the gas concentrations for the interior and the exterior are determined by the same sensor.

It should be emphasized once again that values representing the exterior concentration and the interior concentration, referred to in the following as exterior value and interior value, might of course also be determined instead of the exterior concentration and the interior concentration in all embodiments of the present invention.

DETAILED DESCRIPTION

Detection of an excessive carbon dioxide level (or even of another harmful substance component in the air) in the exterior air is provided via a carbon dioxide sensor mounted in the interior of the vehicle. The same sensor is used for determining the exterior air quality (i.e., of the $CO_2$ level in the exterior air) in fresh air mode and the interior air quality (i.e., of the $CO_2$ level in the interior air). When harmful gases are detected in normal driving operation and in fresh air mode of the vehicle ventilation system or air conditioning system, the carbon dioxide concentration in the exterior air may rise rapidly, for example, in the event of heavy traffic, stop-and-go traffic, or a traffic jam. In recirculating mode of the vehicle ventilation system or air conditioning system, the carbon dioxide concentration in the interior of the vehicle may rise slowly as a function of the number of persons in the vehicle.

In fresh air mode under heavy traffic conditions, the carbon dioxide level in the exterior air and thus also in the interior of the vehicle may rise rapidly.

Figure 1:
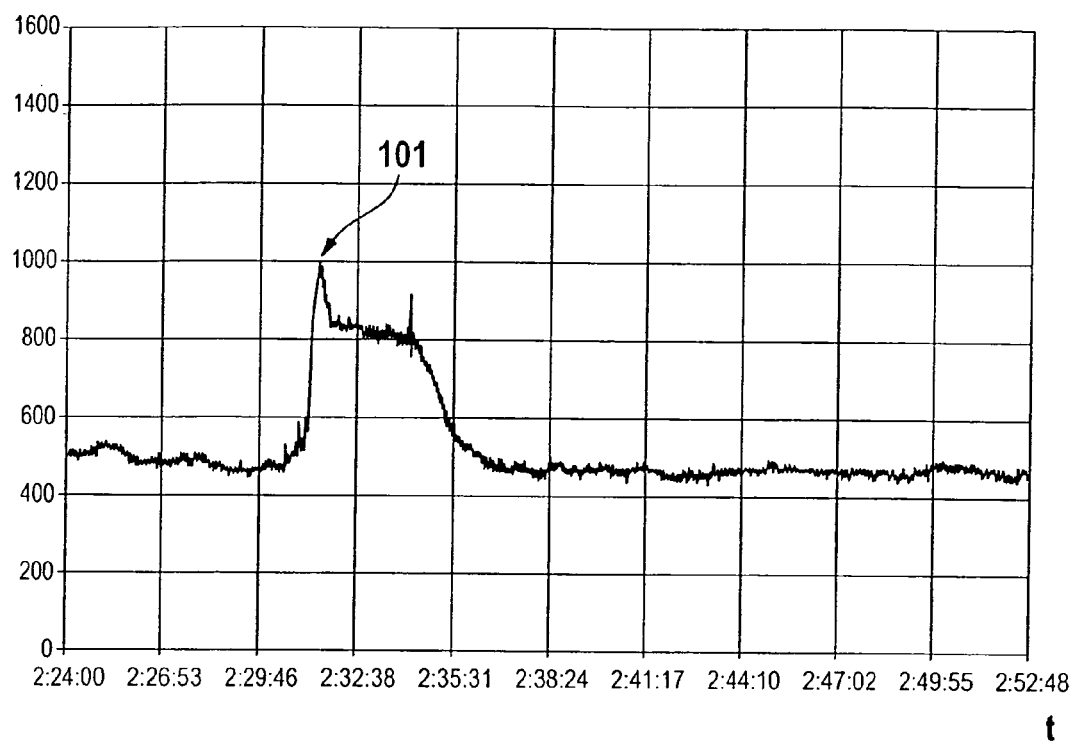
FIG. 1 shows a measured curve recorded in fresh air mode.

FIG. 1 shows a measured curve recorded in fresh air mode in which time t is plotted on the abscissa and the carbon dioxide concentration in the interior on the ordinate in ppm (parts per million). The time on the abscissa is captioned using the notation hours:minutes:seconds. From FIG. 1 it is evident that in fresh air mode the carbon dioxide concentration in the interior of the vehicle increases to 1000 ppm (see caption 101) in 30 seconds. In addition, often a high concentration of other harmful gases such as NO and CO also occurs at the same time, which also results in an additional unpleasant odor. These gases may be prevented from penetrating into the interior of the vehicle by appropriately switching the recirculating flap. This prevents a negative effect on the occupants of the vehicle. The measured curve was recorded during stop-and-go traffic; the sudden rise comes from a truck being directly in front of the measured vehicle at this time.

Figure 2:
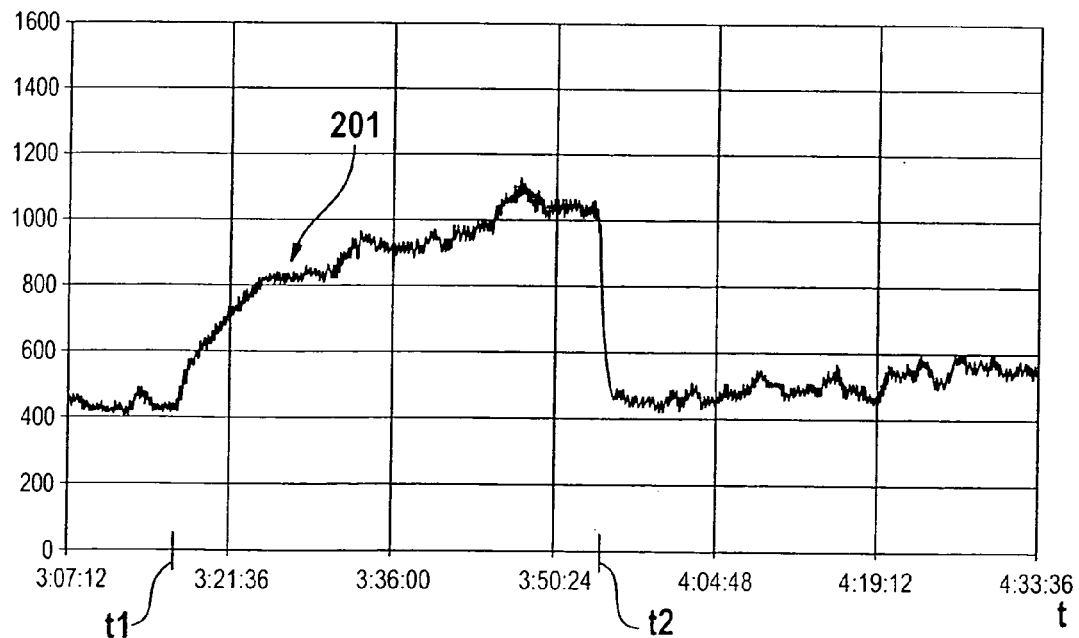
FIG. 2 shows a measured curve recorded in recirculating mode.

FIG. 2 shows a measured curve recorded in recirculating mode in which time t is plotted on the abscissa and the carbon dioxide concentration in the interior on the ordinate in ppm (parts per million). The time on the abscissa is again captioned using the notation hours:minutes:seconds. At time t1, the ventilation system is switched over from "fresh air" to "circulating air"; i.e., the recirculating flap is closed. In recirculating mode the carbon dioxide concentration increases in the vehicle. Here it takes approximately 30 minutes until a carbon dioxide concentration of 1000 ppm is attained in the interior of the vehicle (this time depends on the number of occupants in the vehicle). At time t2, the recirculating flap is opened again, the ventilation system from this time on is in fresh air mode, and the carbon dioxide concentration decreases rapidly.

To detect the carbon dioxide concentration, a carbon dioxide sensor is positioned in the air conditioning or ventilation system of the vehicle in such a way that it is located at a point in the path of both the fresh air flow (in fresh air mode) and the circulating air flow (in recirculating mode). The mixing box (or mixing chamber) of the air conditioning system's or the ventilation system's air distribution unit is particularly well suited for this purpose. The sensor thus determines the carbon dioxide level in the exterior air in fresh air mode, and the carbon dioxide level in the interior air in recirculating mode.

Figure 3:
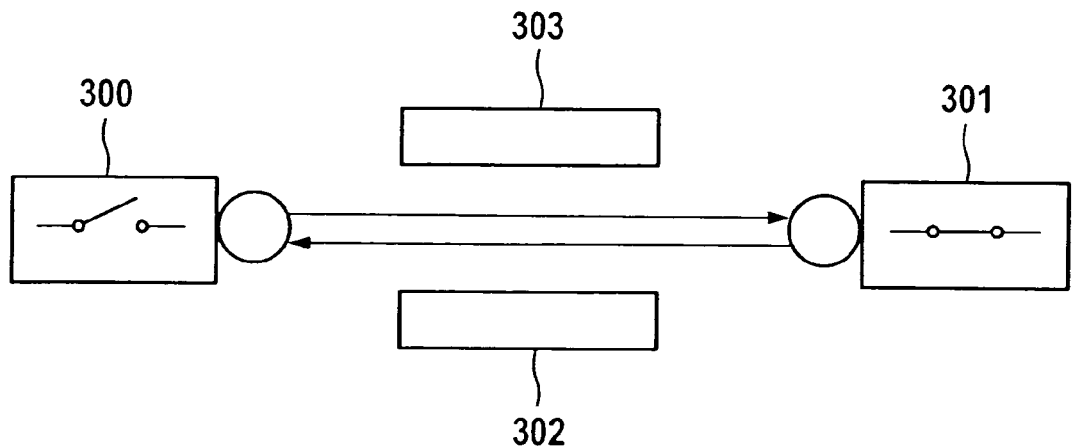
FIG. 3 schematically shows an exemplary method according to the present invention.

FIG. 3 schematically shows a flow chart for the sequence of an exemplary method according to the present invention. An air conditioning system is assumed here for the sake of simplicity. However, the exemplary method is suited, without limitation, also for a vehicle without an air conditioning system, which is only equipped with a ventilation system.

Block 300: The recirculating flap is closed, i.e., the air conditioning system (or the ventilation system) is operating in fresh air mode Block 301: The recirculating flap is open, i.e., the air conditioning system (or the ventilation system) is operating in recirculating mode.

Switchover queries take place in blocks 302 and 303. If the conditions queried there are met, the recirculating flap is switched over to the other state. For example, the carbon dioxide concentration in the air flowing through the mixing box (i.e., the circulating air when the recirculating flap is open and the fresh air when the recirculating flap is closed) may be queried there.

EXAMPLE

1. Assume that the air conditioning system is in recirculating mode 300.
2. A query 303 is made regularly to see whether the carbon dioxide concentration in the circulating air (i.e., the air in the interior of the vehicle) has exceeded a predefined limiting value.
3. As soon as this limiting value is exceeded, the recirculating flap is switched over to fresh air mode 301. A drop in the carbon dioxide concentration in the air in the interior of the vehicle is achieved via the incoming fresh air flow.
4. The air conditioning system is now in fresh air mode 300.
5. A query 302 is now made regularly to see whether the carbon dioxide concentration in the fresh air (i.e., the air in the surroundings of the vehicle) has exceeded a predefined limiting value.
6. As soon as this limiting value is exceeded, the recirculating flap is switched over to recirculating mode 300. This is to prevent fresh air having a high carbon dioxide level from being supplied into the vehicle.

In the case where both the air in the interior of the vehicle and the exterior air assume a value exceeding the particular limiting value (this may be recognized by the position of the recirculating flap changing in rapid succession), the recirculating flap may be brought into the position permitting the better air quality. For this purpose, a query may be made for the additional condition of whether two immediately successive switchover operations of the recirculating flap have taken place. If this is the case, the recirculating flap is brought into the position where the carbon dioxide sensor has determined the lower value. It is now possible to check at regular intervals by briefly switching over the recirculating flap whether the air quality in the other position has improved in the meantime. If so, the recirculating flap is then brought into the other position.

Figure 4:
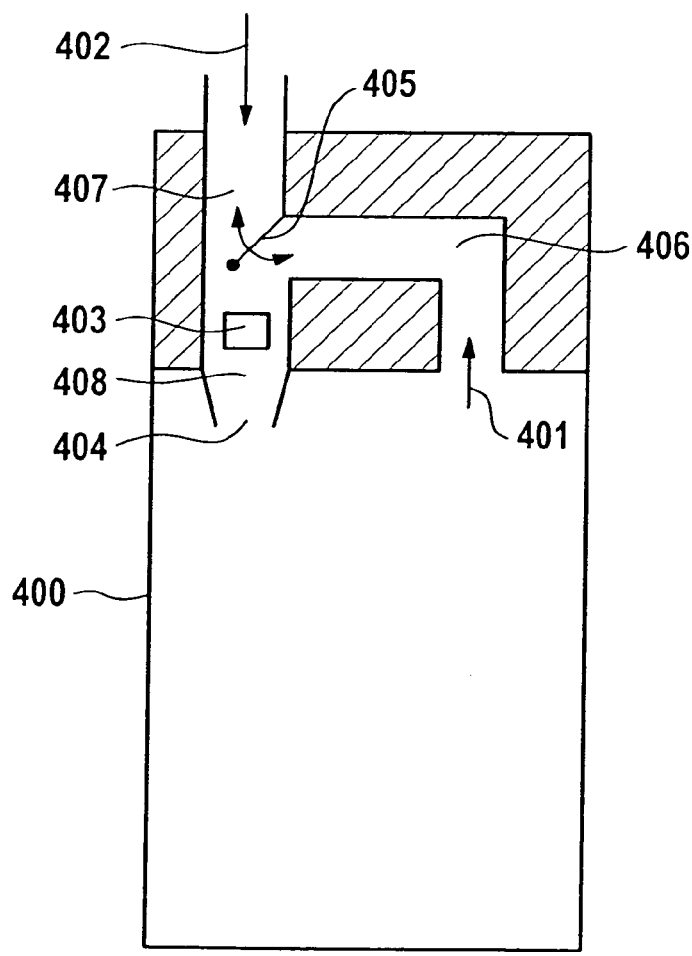
FIG. 4 schematically shows an exemplary embodiment of the device according to the present invention.

FIG. 4 schematically shows a top view of interior 400 of a motor vehicle. In recirculating mode via circulating air duct 406, air is removed from the interior via interior air outlet 401. Inlet 402 for the exterior air into the interior of the vehicle is used in fresh air mode and conducts fresh exterior air into fresh air channel 407. Both air flows meet in mixing chamber 403. Either circulating air duct 406 or fresh air duct 407 may be closed by movable recirculating flap 405 (movable in the direction of the arrows). Gas sensor 403 is located in the mixing box; its output signals are used to control the position of recirculating flap 405. Air inlet 404 of the mixing chamber in the vehicle interior is used for either
- supplying fresh air coming from the outside into the interior of the vehicle; or
- supplying the interior air removed from the vehicle back into the interior of the vehicle.

An intermediary position of the recirculating flap also allows, of course, fresh air and circulating air to be mixed.

What is claimed is:

1. A device for controlling a ventilation system in the interior of a motor vehicle, comprising:
   a gas concentration determining arrangement to determine an exterior value representing an exterior concentration of a gas in exterior air surrounding the vehicle, and to determine an interior value representing an interior concentration of the same gas in the air contained in the interior of the vehicle; and
   an air flow control arrangement, via which a proportion of circulating air and a proportion of fresh air from the exterior of the vehicle in the air delivered to the interior by the ventilation system are controlled as a function of a determined interior value or a determined exterior value;
   wherein the gas concentration determining arrangement consists of a single gas sensor, and
   wherein the gas sensor is in a part of the ventilation system, through which fresh air is suppliable to the interior of the vehicle in a fresh air mode and circulating air is circulatable in the vehicle in a recirculating mode flow.

2. The device of claim 1, wherein the gas sensor is situated in a mixing chamber of the ventilation system.

3. The device of claim 1, wherein the air flow control arrangement includes a recirculating flap.

4. The device of claim 1, wherein the gas sensor includes a carbon dioxide sensor.

5. The device of claim 1, wherein the gas sensor is situated so that it determines the interior value in a recirculating mode of the ventilation system, and determines the exterior value in a fresh air mode of the ventilation system.

6. The device of claim 5, further comprising:
   a query arrangement via which at least the determined interior value is analyzed in the recirculating mode of the ventilation system and, as a function thereof, either the recirculating mode of the ventilation system is maintained or the ventilation system is switched over to the fresh air mode, and via which at least the determined exterior value is analyzed in the fresh air mode of the ventilation system and, as a function thereof, either the fresh air mode of the ventilation system is maintained or the ventilation system is switched over to the recirculating mode.

7. The device of claim 6, wherein:
   in the recirculating mode, the ventilation system is switched over to the fresh air mode if the query arrangement determines that a first limiting value has been exceeded by the interior value, and
   in the fresh air mode, the ventilation system is switched over to the recirculating mode if the query arrangement determines that a second limiting value has been exceeded by the exterior value.

8. The device of claim 7, wherein:
   if in the recirculating mode it is established that the first limiting value has been exceeded by the interior value and immediately in the following fresh air mode it is established that the second limiting value has been exceeded by the exterior value, or
   if in the fresh air mode it is established that the second limiting value has been exceeded by the exterior value and immediately in the following recirculating mode it is established that the first limiting value has been exceeded by the interior value,
   then the ventilation system is switched to the fresh air mode if the determined exterior value is less than the determined interior value, and is switched to the recirculating mode if the determined interior value is less than the determined exterior value, and it remains in this operating state for a predefined time period.

9. A method for controlling an air conditioning system or a ventilation system in a motor vehicle, the method comprising:
   determining an exterior value representing an exterior concentration of a gas in exterior air surrounding the vehicle;

determining an interior value representing an interior concentration of the same gas in an interior of the vehicle; and controlling a proportion of circulating air and a proportion of fresh air from the exterior of the vehicle in the air delivered to the interior by the ventilation system as a function of a determined interior value or a determined exterior value;

wherein gas concentrations for the interior and the exterior are determined by the same sensor, and wherein the sensor is in a part of the ventilation system, through which fresh air is suppliable to the interior of the vehicle in a fresh air mode and circulating air is circulatable in the vehicle in a recirculating mode flow.

10. A device for controlling a ventilation system in the interior of a motor vehicle, comprising:

a gas concentration determining arrangement to determine an exterior value representing an exterior concentration of a gas in exterior air surrounding the vehicle, and to determine an interior value representing an interior concentration of the same gas in the air contained in the interior of the vehicle; and an air flow control arrangement, via which a proportion of circulating air and a proportion of fresh air from the exterior of the vehicle in the air delivered to the interior by the ventilation system are controlled as a function of a determined interior value or a determined exterior value;

wherein the gas concentration determining arrangement consists of a single gas sensor, wherein the gas sensor is situated in a part of the ventilation system, through which fresh air suppliable to the interior of the vehicle in a fresh air mode and circulating air circulatable in the vehicle in a recirculating mode flow, and wherein the gas sensor samples the exterior air surrounding the vehicle and the air contained in the interior of the vehicle in the part of the ventilation system, through which fresh air is supplied to the interior of the vehicle in the fresh air mode and air is circulated in a recirculating mode flow.

* * * * *